US007704908B2

(12) United States Patent
Matusz et al.

(10) Patent No.: US 7,704,908 B2
(45) Date of Patent: Apr. 27, 2010

(54) METHOD FOR REUSING RHENIUM FROM A DONOR SPENT EPOXIDATION CATALYST

(75) Inventors: Marek Matusz, Houston, TX (US); Richard Anthony Fragnito, Humble, TX (US)

(73) Assignee: Shell Oil Company, Houston, TX (US)

( * ) Notice: Subject to any disclaimer, the term of this patent is extended or adjusted under 35 U.S.C. 154(b) by 623 days.

(21) Appl. No.: 11/613,862

(22) Filed: Dec. 20, 2006

(65) Prior Publication Data

US 2007/0203351 A1 Aug. 30, 2007

Related U.S. Application Data

(60) Provisional application No. 60/752,977, filed on Dec. 22, 2005.

(51) Int. Cl.
*B01J 38/48* (2006.01)

(52) U.S. Cl. ....................................................... 502/22

(58) Field of Classification Search ................... 502/22
See application file for complete search history.

(56) References Cited

U.S. PATENT DOCUMENTS

| 3,119,837 | A | 1/1964 | Kingsley et al. ......... 260/348.5 |
| 3,518,285 | A | 6/1970 | Fenton et al. ............ 260/348.5 |
| 3,644,432 | A | 2/1972 | Hoch et al. ................. 260/348 |
| 3,948,621 | A | 4/1976 | Cocuzza et al. ................ 55/29 |
| 4,033,903 | A | 7/1977 | Maxwell ...................... 252/476 |
| 4,125,480 | A | 11/1978 | Maxwell ...................... 252/414 |
| 4,186,106 | A | 1/1980 | Rebsdat et al. .............. 252/414 |
| 4,221,727 | A | 9/1980 | Tsang et al. ............ 260/348.37 |
| 4,249,917 | A | 2/1981 | Tarancon ........................ 55/48 |
| 4,278,562 | A | 7/1981 | Mross et al. ................. 252/430 |
| 4,324,699 | A | 4/1982 | Mross et al. ................. 252/463 |
| 4,361,504 | A | 11/1982 | Solomon et al. ............ 252/463 |
| 4,366,092 | A | 12/1982 | Winterton ................... 252/476 |
| 4,491,638 | A | 1/1985 | Busse ........................... 502/167 |
| 4,529,714 | A | 7/1985 | Mross et al. .................. 502/25 |
| 4,808,738 | A | 2/1989 | Lauritzen ................... 549/536 |
| 4,822,900 | A | 4/1989 | Hayden ....................... 549/534 |
| 4,845,296 | A | 7/1989 | Ahmed et al. ............... 564/477 |
| 4,875,909 | A | 10/1989 | Kakimoto et al. ............. 55/40 |
| 5,187,140 | A | 2/1993 | Thorsteinson et al. ....... 502/348 |
| 5,380,697 | A | 1/1995 | Matsuz et al. ............... 502/348 |
| 5,384,418 | A | 1/1995 | Zajacek et al. .............. 549/531 |
| 5,589,142 | A | 12/1996 | Gribbon ...................... 422/171 |
| 5,618,954 | A | 4/1997 | Boeck et al. ................. 549/534 |
| 5,739,075 | A | 4/1998 | Matusz ....................... 502/302 |
| 5,753,197 | A | 5/1998 | Chen et al. ................. 423/210 |
| 5,801,259 | A | 9/1998 | Kowaleski .................. 549/536 |
| 5,905,161 | A | 5/1999 | Boeck et al. ................. 549/534 |
| 6,080,897 | A | 6/2000 | Kawabe ....................... 568/858 |
| 6,124,508 | A | 9/2000 | Van Kruchten ............. 568/867 |
| 6,228,434 | B1 | 5/2001 | Affinito ....................... 427/488 |
| 6,261,093 | B1 | 7/2001 | Matros et al. ............... 432/181 |
| 6,284,217 | B1 | 9/2001 | Wang et al. ................. 423/651 |
| 6,368,998 | B1 | 4/2002 | Lockemeyer ............... 502/347 |
| 6,380,119 | B1 | 4/2002 | Grosch et al. ................ 502/49 |
| 6,440,895 | B1 | 8/2002 | Tonkovich et al. .......... 502/439 |
| 6,451,864 | B1 | 9/2002 | Wang et al. ................. 518/715 |
| 6,455,713 | B1 | 9/2002 | Monnier ..................... 549/536 |
| 6,491,880 | B1 | 12/2002 | Wang et al. ................. 422/211 |
| 6,494,614 | B1 | 12/2002 | Bennett et al. ............. 366/336 |
| 6,508,862 | B1 | 1/2003 | Tonkovich et al. ........... 95/106 |
| 6,666,909 | B1 | 12/2003 | TeGrotenhuis et al. ....... 95/273 |
| 6,710,002 | B2 | 3/2004 | Grosch et al. ................ 502/49 |
| 6,811,829 | B2 | 11/2004 | Affinito et al. ............. 427/488 |
| 6,851,171 | B2 | 2/2005 | Schmitt ......................... 29/469 |
| 7,005,015 | B2 | 2/2006 | Burgel et al. ............... 148/428 |
| 7,102,022 | B2 | 9/2006 | Evans et al. ................ 549/536 |

FOREIGN PATENT DOCUMENTS

| CA | 1165264 | 4/1984 |
| DE | 258514 A3 | 7/1988 |
| DE | 288055 A7 | 3/1991 |
| EP | 0003642 | 8/1979 |
| EP | 0015649 | 9/1980 |
| EP | 0156447 | 10/1985 |
| EP | 0156448 | 10/1985 |
| EP | 0160330 | 11/1985 |
| EP | 0211521 | 2/1987 |
| EP | 266 015 | 5/1988 |
| EP | 0266015 | 5/1988 |

(Continued)

OTHER PUBLICATIONS

Journal of the American Chemical Society 60 (1938) pp. 309-316.
Kirk-Othmer Encyclopedia of Chemical Technology, 3rd edition, vol. 9, 1980, pp. 445 to 447.
Research Disclosure No. 465117, Research Disclosure Journal, Jan. 2003, p. 106, Kenneth Mason Publications Ltd.
Reverse-Flow Operation in Fixed Bed Catalytic Reactors, Cata. Rev.-Sci. Eng., 28(1), 1-68 (1996).
T. Nishikubo, A. Kameyama, J. Yamashita and M. Tomoi, Journal of Polymer Science, Pt. A. Polymer Chemist, 31, 939-947 (1993).
Kirk-Othmer, Concise Encyclopedia of Chemical Technology (4th Ed. 1999) pp. 1759-1760.

(Continued)

*Primary Examiner*—Taofiq A Solola

(57) ABSTRACT

A method for reusing rhenium from a donor spent epoxidation catalyst, the method comprising: providing a donor comprising spent epoxidation catalyst comprising rhenium, the donor having a cumulative alkylene oxide production of 0.16 $kT/m^3$ of the spent epoxidation catalyst or more; contacting the donor with an aqueous liquid to produce rhenium-depleted donor and aqueous extract comprising extracted rhenium; separating the aqueous extract and the rhenium-depleted donor; and, using the extracted rhenium as a source of rhenium in a subsequent process.

27 Claims, No Drawings

FOREIGN PATENT DOCUMENTS

| | | |
|---|---|---|
| EP | 0318099 | 5/1989 |
| EP | 0352850 | 1/1990 |
| EP | 0529726 | 3/1993 |
| EP | 568407 | 11/1993 |
| EP | 0705826 | 4/1996 |
| EP | 0893443 | 1/1999 |
| EP | 0776890 | 1/2001 |
| EP | 0918762 | 5/2001 |
| EP | 1314473 | 5/2003 |
| EP | 1073649 | 9/2003 |
| EP | 1283747 | 3/2004 |
| EP | 1115484 | 6/2004 |
| EP | 1426106 | 6/2004 |
| GB | 1413251 | 11/1975 |
| GB | 1435848 | 5/1976 |
| JP | 56/92228 | 7/1981 |
| WO | 95/20559 | 8/1995 |
| WO | 96/17811 | 6/1996 |
| WO | 98/00413 | 1/1998 |
| WO | 98/00414 | 1/1998 |
| WO | 98/00415 | 1/1998 |
| WO | 00/15332 | 3/2000 |
| WO | 01/12312 | 2/2001 |
| WO | 01/41926 | 6/2001 |
| WO | 01/54812 | 8/2001 |
| WO | 2004/099113 | 11/2004 |
| WO | WO2004101144 | 11/2004 |
| WO | 2005/032693 | 4/2005 |
| WO | WO2005097318 | 10/2005 |
| WO | 2006/102189 | 9/2006 |

OTHER PUBLICATIONS

Cowell, J. J., Santra, A. K., and Lambert, R. M., "Ultraselective Epoxidation of Butadiene on Cu{111} and the Effects of Cs Promotion," Journal of the American Chemical Society, vol. 122, No. 10, Mar. 15, 2000, pp. 2381-2382.

Monnier, J. R., Stavinoha, J. L., Jr., and Minga, R. L., "Stability and Distribution of Cesium in Cs-promoted Silver Catalysts Used for Butadiene Epoxidation," Journal of Catalysis, 226 (2004), pp. 401-409.

Monnier, J. R., Stavinoha, J. L., Jr., and Hartley, G. W., "Effects of Chlorine and Chlorine Dynamics During Silver-Catalyzed Epoxidation of Butadiene," Journal of Catalysis, 226 (2004), pp. 321-333.

Dioos, Bart M. L. and Jacobs, Pierre A., "$Cr^{III}$(Salen) Impregnated on Silica for Asymmetric Ring Opening Reactions and its Recovery via Desorption/Re-Impregnation," Tetrahedron Letters 44 (2003) pp. 8815-8817.

METHOD FOR REUSING RHENIUM FROM A DONOR SPENT EPOXIDATION CATALYST

CROSS-REFERENCE TO RELATED APPLICATION

This application claims the benefit of U.S. Provisional Application No. 60/752,977 filed Dec. 22, 2005 the entire disclosure of which is hereby incorporated by reference.

FIELD OF THE INVENTION

The present application relates to a method of reusing rhenium from a donor spent epoxidation catalyst.

BACKGROUND OF THE INVENTION

Rhenium is a precious metal which is extremely costly. Rhenium has a wide variety of uses. One use for rhenium is as a promoter on an epoxidation catalyst.

U.S. Pat. No. 5,739,075 (the '075 patent) describes a process for the preparation of silver-containing catalysts suitable for the preparation of ethylene oxide. The process deposits a number of materials, including silver and a promoting amount of rhenium, on a porous refractory support. The '075 patent also describes rhenium compounds that may be solubilized for deposition on a support. See col. 13, ll. 2-32.

Unfortunately, epoxidation catalysts are subject to a performance decline, which represents itself by a loss in activity of the epoxidation catalyst and a loss in selectivity in the formation of the desired olefin oxide. In response to the loss of activity, the epoxidation reaction temperature may be increased such that the production rate of the olefin oxide is maintained. The operation of commercial reactors is normally limited with respect to the reaction temperature. When the applicable temperature limit has been reached, either the production rate of the olefin oxide is reduced or the production of the olefin oxide is interrupted to exchange the existing charge of epoxidation catalyst for a fresh charge. A fresh charge of catalyst comprising rhenium is very expensive.

Some efforts have been made to regenerate epoxidation catalysts. For example, U.S. Pat. No. 4,529,714 describes a process for regenerating silver-containing carrier catalysts used in the preparation of ethylene oxide which comprises treating a deactivated catalyst with a solution comprising a potassium, rubidium, or cesium component and a reducing agent.

A need exists for methods which reduce the cost of using rhenium as a promoter component on epoxidation catalysts.

SUMMARY OF THE INVENTION

The present invention provides a method for reusing rhenium from a donor comprising spent epoxidation catalyst.

The present invention also provides a method for preparing an epoxidation catalyst comprising rhenium recovered from a donor comprising spent epoxidation catalyst.

The present invention provides a method for reusing rhenium from a donor spent epoxidation catalyst, the method comprising: providing a donor comprising spent epoxidation catalyst comprising rhenium, the donor having a cumulative alkylene oxide production of 0.16 kilotons ("kT")/m$^3$ of the spent epoxidation catalyst or more; contacting the donor with an aqueous liquid to produce rhenium-depleted donor and aqueous extract comprising extracted rhenium; separating the aqueous extract and the rhenium-depleted donor; and, using the extracted rhenium as a source of rhenium in a subsequent process.

The present invention also provides a process for the epoxidation of one or more olefins comprising reacting a feed comprising one or more olefins in the presence of an epoxidation catalyst prepared according to the present invention.

The present invention also provides a process for the production of a 1,2-diol, a 1,2-diol ether, a 1,2-carbonate, or an alkanol amine, the process comprising converting an olefin oxide into the 1,2-diol, the 1,2-diol ether, the 1,2-carbonate, or the alkanol amine wherein the olefin oxide has been obtained by a process for the epoxidation of one or more olefins in the presence of an epoxidation catalyst prepared according to the present invention.

DETAILED DESCRIPTION OF THE INVENTION

The present application provides a process for reducing the cost of using rhenium as a promoter component on epoxidation catalysts.

In one embodiment, the process advantageously recovers and reuses rhenium from a donor spent epoxidation catalyst.

In one embodiment, a deposition mixture comprising an aqueous extract from the rhenium recovery process is used to deposit the extracted rhenium on a donee. In this embodiment, the donee may be fresh carrier material or spent epoxidation catalyst.

In one embodiment, the extracted rhenium is separated from the aqueous extract produced during the rhenium recovery method. The separated rhenium, referred to as "recovered rhenium", may be used for a variety of purposes. In one embodiment, the recovered rhenium is a stand alone product. In one embodiment, the recovered rhenium is used to produce a deposition mixture to deposit recovered rhenium on a donee. In one embodiment, the donee may be fresh carrier material or spent epoxidation catalyst.

The process has the advantage that it can reduce the need to dispose of an aqueous liquid used to wash spent epoxidation catalyst, thereby reducing disposal and environmental costs.

The process also has the advantage of reducing the cost of obtaining fresh rhenium or fresh catalyst comprising rhenium.

The Spent Epoxidation Catalyst

The rhenium recovery method of the present application may be used to recover rhenium from a variety of spent epoxidation catalysts comprising rhenium. In one embodiment, the spent epoxidation catalyst comprises a carrier material comprising a base amount of one or more Group 11 metals. In an advantageous embodiment, the Group 11 metal is silver. In one embodiment, the spent epoxidation catalyst comprises one or more of rhenium, rhenium copromoters, and/or one or more further elements, as described below.

The word "dopants" is sometimes collectively used herein to refer to rhenium, one or more Group 11 metals, one or more rhenium copromoters, and to any further elements that are deposited on a donee carrier material or on a donee spent epoxidation catalyst.

Typically, the epoxidation catalyst is solid under the conditions of the epoxidation reaction. After an epoxidation reaction has been run for a prolonged period of time, the epoxidation catalyst becomes spent. As used herein, a "spent" epoxidation catalyst refers to an epoxidation catalyst having a cumulative alkylene oxide production of 0.16 kilotons ("kT")/m$^3$ of the spent epoxidation catalyst or more.

The activity and/or selectivity of an epoxidation catalyst generally decreases with an increase in cumulative alkylene oxide production. In one embodiment, the cumulative alkylene oxide production is 0.2 kT/m$^3$ of the spent epoxidation catalyst or more. In one embodiment, the cumulative alkylene oxide production is 0.3 kT/m$^3$ of the spent epoxidation catalyst or more. In one embodiment, the cumulative alkylene oxide production is 0.45 kT/m$^3$ of the spent epoxidation catalyst or more. In one embodiment, the cumulative alkylene oxide production is 0.7 kT/m$^3$ of the spent epoxidation catalyst or more. In one embodiment, the cumulative alkylene oxide production is 1 kT/m$^3$ of the spent epoxidation catalyst or more.

In some embodiments, a spent epoxidation catalyst is a catalyst which, when fresh, exhibits an initial activity and an initial selectivity under initial conditions, and the spent epoxidation catalyst exhibits one or more performance decline selected from the group consisting of (a) a 2% or more reduction in selectivity compared to the initial selectivity under the initial conditions, and (b) a 10° C. or more reduction in activity compared to the initial activity under the initial conditions. In this context, prolonged use is not the only reason why the catalyst may become "spent." For example, a "spent" epoxidation catalyst may have been poisoned or otherwise deactivated. In an advantageous embodiment, the "spent" epoxidation catalyst has reduced activity and/or selectivity because of a relatively large cumulative alkylene oxide production.

In particular embodiments, the spent epoxidation catalyst exhibits a 5% or greater reduction in selectivity compared to the initial selectivity under the initial conditions. In another embodiment, the spent epoxidation catalyst exhibits an 8% or greater reduction in selectivity compared to the initial selectivity under the initial conditions. In another embodiment, the spent epoxidation catalyst exhibits a 10% or greater reduction in selectivity compared to the initial selectivity under the initial conditions.

Once an epoxidation catalyst becomes spent, the spent epoxidation catalyst may be subjected to the rhenium recovery method of the present application.

The Rhenium Recovery Method

In the present application, the word "extract," or a derivative thereof, is sometimes used with reference to the rhenium recovery method. The word "extract" or derivative thereof is used for convenience only. Unless expressly stated, the use of the word "extract" or derivative thereof should not be construed as limiting the method by which the rhenium is recovered.

The rhenium recovery method comprises providing a donor spent epoxidation catalyst comprising a quantity of rhenium, contacting the donor spent epoxidation catalyst with an amount of aqueous liquid at a temperature sufficiently high and for a period of time sufficient to produce a rhenium-depleted donor and an aqueous extract comprising extracted rhenium. The procedure may be repeated, for example, one or more additional times.

In one embodiment, a combination of one or more aqueous extracts from the rhenium recovery process comprises a majority of the quantity of rhenium initially present on the donor. In one embodiment, a combination of the one or more aqueous extracts from the rhenium recovery process comprises 75% w or more of the quantity of rhenium initially present on the donor. In one embodiment, a combination of the one or more aqueous extracts from the rhenium recovery process comprises 85% w or more of the quantity of rhenium initially present on the donor.

Contacting the donor with the aqueous liquid generally occurs at an elevated temperature. The elevated temperature generally is sufficient to facilitate the recovery of rhenium from the donor catalyst. In one embodiment, the aqueous liquid is just water. In one embodiment, the elevated temperature is 50° C. or more. In one embodiment, the elevated temperature is 100° C. or less. The mixture is heated for a period of time effective to recover at least a portion of the rhenium from the donor and to produce an aqueous extract comprising extracted rhenium.

The heated mixture is allowed to cool. Suitable cool down temperatures are sufficiently low to safely separate the aqueous extract from the rhenium-depleted donor. In one embodiment, the cool-down temperature is 60° C. or less. In one embodiment the cool-down temperature is 55° C. or less. In one embodiment, the cool-down temperature is 50° C. or less.

Once the heated mixture has cooled sufficiently, the aqueous extract is recovered. In one embodiment, the aqueous extract is simply decanted from the rhenium-depleted donor. Depending upon the volume of water and the % recovery desired, the procedure may be repeated.

In one embodiment, the weight of aqueous liquid used to recover rhenium is substantially the same as the weight of the donor from which rhenium is recovered. In this embodiment, it may be desirable to perform multiple extractions. This embodiment requires more time and labor to perform the 1:1 w/w extraction. The embodiment has the advantage, however, that three 1:1 w/w extractions typically can recover most, if not substantially all, of the rhenium initially present on the donor in a relatively concentrated aqueous extract.

In one embodiment, an excess of the aqueous liquid is used. Suitable amounts may vary. For example, the excess may be 2:1 w/w or more aqueous liquid to donor spent epoxidation catalyst. In this embodiment, fewer extractions recover larger relative amounts of rhenium, but a more dilute extract is produced. This embodiment therefore is a less preferred embodiment since it requires more equipment and labor to handle more diluent.

Suitable aqueous liquids include just water. Suitable aqueous liquids also may comprise additives. Suitable additives include, for example, salts, acids, bases, peroxides, organic diluents, and the like.

Suitable salts for inclusion in an aqueous solution include, for example, ammonium salts and halide salts of alkali metals.

Suitable ammonium salts include, for example, ammonium nitrates, ammonium acetates, ammonium carboxylates, ammonium oxalates, ammonium citrates, ammonium fluorides, and combinations thereof. Suitable salts also include other types of nitrates, for example, alkali metal nitrates, such as lithium nitrate. Suitable halide salts of alkali metals include, for example, sodium chloride, sodium bromide, sodium iodide, potassium chloride, potassium bromide, potassium iodide, lithium chloride, lithium bromide, lithium iodide, cesium chloride, cesium bromide, cesium iodide, rubidium chloride, rubidium bromide, rubidium iodide, and combinations thereof.

Suitable organic diluents for inclusion in the aqueous liquid include, for example, one or more of methanol, ethanol, propanol, isopropanol, tetrahydrofuran, ethylene glycol, ethylene glycol dimethyl ether, diethylene glycol dimethyl ether, dimethylformamide, acetone, or methyl ethyl ketone.

Suitable acids include, for example, nitric acid, carbonic acid, acid halides, sulfuric acid, carboxylic acids, citric acid, lactic acid, oxalic acid, acetic acid, and combinations thereof. Examples of suitable bases include, for example, alkali metal hydroxides, ammonium hydroxide, alkyl ammonium hydroxides, and combinations thereof. Suitable alkali metal hydroxides include, for example, cesium hydroxide, potassium hydroxide, lithium hydroxide, sodium hydroxide, and combinations thereof.

In one embodiment, the aqueous liquid is an aqueous ammonium nitrate solution. In an advantageous embodiment, the aqueous liquid is just water. Where the aqueous liquid is just water, the water advantageously may be deionized water.

The method of recovering rhenium from the donor spent epoxidation catalyst can be a batch process. In one embodiment, the method is a continuous extraction process. In one embodiment, the method is performed using countercurrent extraction. A person skilled in the art will recognize many suitable variations of such procedures.

In one embodiment, the extracted rhenium present in the aqueous extract is used as a source of rhenium in a subsequent process. In one embodiment, the extracted rhenium is separated from the aqueous extract to produce recovered rhenium, and the recovered rhenium is used as a source of rhenium in a subsequent process.

Separation of Extracted Rhenium to Produce Recovered Rhenium

In order to produce recovered rhenium, the extracted rhenium may be separated from the aqueous extract using any suitable separation method. In one embodiment, the extracted rhenium is separated from the aqueous extract by contacting the aqueous extract with an ion exchange resin bed. In another embodiment, the aqueous portion of the aqueous extract may be removed, for example, by a process selected from the group consisting of sublimation, distillation, concentration, and combinations thereof. For purposes of illustration only, the foregoing methods are described in more detail below.

Contacting the Aqueous Extract with an Ion Exchange Resin Bed

In one embodiment, the aqueous extract is passed through an ion exchange resin bed and the recovered rhenium is separated by washing the resin bed with appropriate reagent. Suitable reagents include, for example, aqueous acidic solutions. Examples of suitable acids for use in the aqueous acidic solutions include, for example, nitric acid, sulfuric acid, hydrochloric acid, and mixtures thereof.

If the aqueous extract is acidic, or if acid is added to render the aqueous extract acidic, then the aqueous extract may be conveniently neutralized to obtain recovered rhenium in the form of soluble rhenium salts. Soluble rhenium salts include, for example ammonium perrhenate, lithium perrhenate, cesium perrhenate, and combinations thereof.

Sublimation and/or Distillation of the Aqueous Extract

In one embodiment, the aqueous portion of the extract is removed by sublimation and/or distillation of the aqueous extract to produce rhenium oxide. See, e.g., Kirk-Othmer, *Concise Encyclopedia of Chemical Technology* (4$^{th}$ Ed. 1999) pp. 1759-1760, incorporated herein by reference. Rhenium oxide obtained in such a process is very pure and may be used in a variety of applications.

In one embodiment, the rhenium oxide obtained by sublimation and/or evaporation is solubilized with water to form perrhenic acid. In one embodiment, the rhenium oxide obtained by sublimation and/or evaporation is solubilized with base to form soluble perrhenate salts.

Concentration or Evaporation of the Aqueous Extract

In one embodiment, the aqueous portion of the aqueous extract is removed by concentration. For example, the aqueous portion of the aqueous extract may be removed by evaporation to produce a desired concentration of rhenium, perrhenic acid, or soluble perrhenate salts. In one embodiment, the concentrated or evaporated aqueous extract is analyzed for rhenium and other components.

Uses for Aqueous Extract and/or Recovered Rhenium

The rhenium that is recovered using the rhenium recovery method may be used in a variety of applications. This is true whether the rhenium is extracted rhenium in the aqueous extract or recovered rhenium. As seen above, recovered rhenium may take a variety of forms. Examples include rhenium oxide and/or a solution comprising rhenium, perrhenic acid, or soluble perrhenate salts.

In one embodiment, recovered rhenium is used as a stand alone product. As a stand alone product, the recovered rhenium and/or a solution comprising the recovered rhenium may, for example, be sold to a rhenium supplier for use in a wide variety of applications.

In one embodiment, the recovered rhenium and/or a solution comprising the recovered rhenium may be used to prepare superalloys and/or protective coatings for superalloys. Superalloys and/or protective coatings for superalloys are used in the construction of components subject to high temperatures during use. An example of such components are various types of turbines. See, e.g., U.S. Pat. No. 7,005,015, entitled "High-temperature-resistant component and process for producing the high-temperature-resistant component," incorporated herein by reference.

Preparation of Epoxidation Catalyst

In one embodiment, the aqueous extract, itself, either is the deposition mixture or is used to prepare a deposition mixture for depositing rhenium on a support. In one embodiment, the support is spent epoxidation catalyst. In another embodiment, the support is carrier material for fresh epoxidation catalyst. In this embodiment, the extracted rhenium is deposited on the donee, and it is not necessary to separate the extracted rhenium from the aqueous extract. This embodiment has the advantage that it is not necessary to process or dispose of the diluent from the aqueous extract because the diluent is used as an integral part of the deposition mixture.

In one embodiment, the deposition mixture comprises an aqueous liquid comprising recovered rhenium.

In one embodiment, in addition to the extracted and/or recovered rhenium, it is advantageous for the deposition mixture also to comprise one or more Group 11 metals. In an advantageous embodiment, the Group 11 metal is silver.

In one embodiment, the deposition mixture further comprises one or more components selected from additional fresh rhenium, Group 11 metal, rhenium copromoters, further elements, and mixtures thereof. In one embodiment, the deposition mixture comprises the aqueous extract comprising extracted rhenium, silver, one or more rhenium copromoters, and/or one or more further elements.

Where the extracted and/or recovered rhenium is used to prepare fresh epoxidation catalyst, the deposition of dopants produces an epoxidation catalyst which is catalytically effective to catalyze the conversion of olefin and oxygen to produce alkylene oxide. Where the extracted and/or recovered rhenium is used to rejuvenate a donee spent epoxidation catalyst, the deposition of dopants produces a rejuvenated epoxidation catalyst which exhibits one or more improvements comprising increased selectivity and increased activity compared to the donee spent epoxidation catalyst.

The deposition mixtures and the deposition methods are described in more detail below.

Deposition Methods

Suitable deposition methods include, for example, impregnation, ion exchange, and the like. Suitable impregnation methods include, for example, vacuum impregnation and pore volume impregnation. In one embodiment, the deposition method is impregnation. In one embodiment, the deposition method is vacuum impregnation.

The rhenium recovery method and/or the deposition methods may be performed inside or outside of an epoxidation reactor. In one embodiment, the rhenium recovery method is performed using countercurrent extraction.

Optional Wash of Donee Spent Epoxidation Catalyst

Where the extracted or recovered rhenium is to be deposited on a donee spent epoxidation catalyst, it is not necessary, but it may be desirable to wash the donee spent epoxidation catalyst before the deposition. Washing of the donee spent epoxidation catalyst generally occurs under conditions effective to remove most of the soluble dopants and/or ionizable materials from the donee spent epoxidation catalyst and to produce washed donee spent epoxidation catalyst.

In one embodiment, the aqueous extract from washing a donor spent epoxidation catalyst may be combined with silver or a silver deposition mixture to produce a combined deposition mixture. In one embodiment, this combined deposition mixture is used to deposit extracted rhenium and silver onto the donor spent epoxidation catalyst, thereby producing a rejuvenated epoxidation catalyst.

Referring again to the wash procedure, the washing reagent may be aqueous liquid. In one embodiment, the aqueous liquid comprises one or more additives, such as salts. Suitable salts for inclusion in the aqueous liquid include, for example, ammonium salts. Suitable ammonium salts include, for example, ammonium nitrates, ammonium acetates, ammonium carboxylates, ammonium oxalates, ammonium citrates, ammonium fluorides, and combinations thereof. Suitable salts also include other types of nitrates, for example, alkali metal nitrates, such as lithium nitrate. In one embodiment, the aqueous liquid comprises one or more organic diluent. Suitable organic diluents for inclusion in the aqueous liquid include, for example, one or more of methanol, ethanol, propanol, isopropanol, tetrahydrofuran, ethylene glycol, ethylene glycol dimethyl ether, diethylene glycol dimethyl ether, dimethylformamide, acetone, methyl ethyl ketone, or mixtures thereof.

In one embodiment, the aqueous liquid is just water. In another embodiment, the aqueous liquid is aqueous ammonium nitrate solution.

Where the donee is washed, the wash may take place at any suitable temperature. In one embodiment, the donee is washed at an elevated temperature, for example, at a temperature of from 30 to 100° C. In one embodiment, the elevated temperature is from 35 to 95° C. The washing may comprise contacting the donee with the aqueous liquid for a period of time.

The contact time is not material as long the contact time is sufficient to remove soluble dopants and/or ionizable materials from the donee. In one embodiment, the contact time may be 24 hours or less. In one embodiment, the contact time may be 10 hours or less. In one embodiment, the contact time is 5 hours or less. In one embodiment, the contact time is 1 hour or more. In one embodiment, the contact time is 0.25 hours or more. In one embodiment, the contact time is 0.05 hours or more.

After the contact time has passed, the liquid comprising materials that have been leached from the donee is removed. The washing may be repeated, for example two or three times, until there is no change in the composition of the effluent. The effluent may be treated and/or separated and/or purified, such that any Group 11 metal and rhenium present in the effluent may be used in subsequent processing. If the donee is washed, then the washed donee may be dried before further treatment by heating at a temperature and for a time sufficient to remove the remaining wash solution.

Drying of the washed donee is not necessary. However, drying typically occurs at a temperature of from 100° C. to 300° C. for a period of time. The period of time is not material. In one embodiment, the drying time is 10 hours or less. In one embodiment, the drying time is 5 hours or less. In one embodiment, the drying time is 0.25 hours or more. In one embodiment, the drying time is 0.05 hours or more. In one embodiment, the catalyst is dried at 250° C. for 15 minutes in a catalyst oven in flowing air.

In one embodiment, a quantity of donee pellets is added to an excess of ammonium nitrate solution to form a slurry. Suitable ammonium nitrate solutions have an ammonium nitrate concentration of 0.001% w or more, based on the total weight of the ammonium nitrate solution. Suitable ammonium nitrate solutions have an ammonium nitrate concentration of 85% w or less on the same basis. In an advantageous embodiment, the ammonium nitrate solution has an ammonium nitrate concentration of 0.03% w on the same basis.

The resulting slurry is heated at an elevated temperature. Suitable temperatures include, for example, from 80° C. to 90° C. In one embodiment, the elevated temperature is maintained for a period of time. A suitable period of time is, for example, 1 hour or more. In one embodiment, the donee pellets are dried before proceeding. In one embodiment, the donee pellets are added to a fresh excess of ammonium nitrate solution and heated again at an elevated temperature of, for example, from 80° C. to 90° C. The temperature is again maintained for a period of time. Thereafter, the ammonium nitrate solution is decanted and the donee pellets are soaked in another excess of ammonium nitrate solution at room temperature (typically from 15° C. to 25° C.). In one embodiment, the room temperature treatment is repeated.

It is not necessary to dry the donee before depositing one or more dopants. In one embodiment, the washed donee is dried, as described previously.

The one or more dopants then may be deposited on a donee using methods known in the art. Reference may be made to U.S. Pat. No. 5,380,697, U.S. Pat. No. 5,739,075, EP-A-266015, and U.S. Pat. No. 6,368,998, which are incorporated herein by reference. In one embodiment, the methods include impregnating the particulate carrier material with a liquid mixture comprising cationic Group 11 metal-amine complex and a reducing agent.

Depositing Extracted or Recovered Rhenium on the Donee

In one embodiment, the recovered rhenium is deposited on a donee selected from the group consisting of fresh catalyst carrier material and spent epoxidation catalyst. The donee may or may not comprise a base amount of rhenium. Where the donee is fresh catalyst carrier material, the donee may not comprise a base amount of rhenium. Where the donee is spent epoxidation catalyst, the donee may comprise a base amount of rhenium. Extracted or recovered rhenium may be deposited on the donee prior to, together with or subsequent to the deposition of the other dopants. Where the extracted or recovered rhenium and Group 11 metal are both deposited, an epoxidation catalyst generally is formed. Where only the extracted or recovered rhenium is deposited, a catalyst precursor to an epoxidation catalyst generally is formed.

General Procedures

In one embodiment, the donee is contacted with a deposition mixture comprising the aqueous extract produced during the recovery of rhenium from one or more donor spent epoxidation catalysts or from the donee epoxidation catalyst, itself. In another embodiment, the donee is contacted with a recovered rhenium deposition mixture prepared using recovered rhenium which has been separated from the aqueous extract recovered during the rhenium recovery method. After the deposition mixture is contacted with the donee for a period of time, the diluent or liquid component is removed, leaving at least a portion of the extracted or recovered rhenium on the donee.

Suitable deposition mixtures for recovered rhenium typically comprise the recovered rhenium dissolved or dispersed in a liquid. Suitable liquids may include, for example, the aqueous extract from the donor or donee spent epoxidation catalyst. Suitable liquids also may include, for example, water or an aqueous organic diluent. Suitable aqueous organic diluents are described above with respect to the wash procedure. The form in which the recovered rhenium may be deposited is not material to the invention. For example, the recovered rhenium may suitably be provided as an oxide or as an oxyanion, for example, as a rhenate or perrhenate, in salt or acid form. An advantageous solution for depositing recovered rhenium is an ammonium perrhenate solution.

In particular embodiments, the recovered rhenium deposition mixture may be kept in contact with the donee for a contact time before removing a liquid component. The duration of the contact time is not material. Suitable contact times are described above in relation to the wash procedure.

In one embodiment, the donee is evacuated for a period of time before contact with one or more deposition mixtures described herein. In one embodiment, the donee is evacuated to less than 760 mm Hg (atmospheric pressure). In one embodiment, the donee is evacuated to 250 mm Hg or less. In one embodiment, the donee is evacuated to 200 mm Hg or less. In one embodiment, the donee is evacuated to 1 mm Hg or more. In one embodiment, the donee is evacuated to 5 mm Hg or more. In one embodiment, the donee is evacuated to 10 mm Hg or more. Advantageously, the donee is evacuated to 20 mm Hg or more.

In one embodiment, the deposition mixture is contacted with the donee after the donee is evacuated. In one embodiment, the vacuum is maintained while the donee is contacted with the deposition mixture. In this embodiment, after contacting the donee with the deposition mixture, the vacuum is released.

Depositing Extracted or Recovered Rhenium on a Carrier Material for a Fresh Epoxidation Catalyst Where the donee is a carrier material for preparing fresh epoxidation catalyst, the amount of extracted or recovered rhenium deposited on the carrier material generally produces a total quantity of rhenium of 250 mmole/kg of the fresh epoxidation catalyst or less. In one embodiment, the total quantity of rhenium is 50 mmole/kg of the fresh epoxidation catalyst or less. In one embodiment, the total quantity of rhenium is 25 mmole/kg of the fresh epoxidation catalyst or less. In one embodiment, the total quantity of rhenium is 15 mmole/kg of the fresh epoxidation catalyst or less. In one embodiment, the total quantity of rhenium is 10 mmole/kg of the fresh epoxidation catalyst or less.

Depositing Extracted or Recovered Rhenium on Donee Spent Epoxidation Catalyst

Where the donee is spent epoxidation catalyst, the components deposited to rejuvenate the spent epoxidation catalyst generally are referred to as either "additional" components or as "rejuvenating" components. This designation distinguishes the additional or rejuvenating component from any base amount of the same component that was initially present on the spent epoxidation catalyst.

Where the donee is spent epoxidation catalyst, the donee may or may not comprise a base amount of rhenium. In order to deposit rejuvenating extracted or recovered rhenium, the donee may be maintained in contact with the deposition mixture for a contact period sufficient to impregnate pores of the donee spent epoxidation catalyst with the deposition mixture, producing an intermediate donee. The specific contact period generally is not material to the impregnation. A suitable contact period is 0.1 minute or more. A typical contact period is 30 seconds or more. As a practical matter, the contact period generally is one minute or more. In one embodiment, the contact period is 3 minutes or more.

After expiration of the contact period, the intermediate donee may be separated from a liquid component using any known method. For example, the liquid component simply may be decanted or drained from the intermediate donee. For more rapid separation, the liquid component may be removed by mechanical means. Suitable mechanical means include shaking, centrifuging, and the like. The intermediate donee may be allowed to dry or may be exposed to drying conditions.

The rhenium deposited on a spent epoxidation catalyst, from whatever source, is sometimes referred to as "rejuvenating rhenium." The amount of rejuvenating rhenium generally is 0.1 mmole/kg or more, based on the weight of the rejuvenated epoxidation catalyst. In one embodiment, the amount of rejuvenating rhenium is 2 mmole/kg or more on the same basis. In one embodiment, the amount of rejuvenating rhenium is 50 mmole/kg or less on the same basis. In one embodiment, the amount of rejuvenating rhenium is 20 mmole/kg or less on the same basis.

The deposition may be carried out more than once, for example two times or three times, to accomplish the deposition of a desired amount of rejuvenating rhenium.

Deposition of Group 11 Metal

The donee may or may not comprise a base amount of one or more Group 11 metals. Where the donee is carrier material for producing fresh epoxidation catalyst, the donee typically does not comprise a base amount of one or more Group 11 metals. Where the donee is spent epoxidation catalyst, the donee typically does comprise a base amount of one or more Group 11 metals.

The one or more Group 11 metals may be selected from the group consisting of silver, gold, and combinations thereof. In one embodiment, the Group 11 metal comprises silver.

Depositing Group 11 Metal on Fresh Epoxidation Catalyst

Fresh epoxidation catalyst exhibits appreciable catalytic activity when the Group 11 metal content is 10 g/kg or more, based on the weight of the fresh epoxidation catalyst, as measured by nitric acid digestion and silver titration. In one embodiment, the Group 11 metal content is 50 g/kg or more on the same basis. In one embodiment, the Group 11 metal content is 100 g/kg or more on the same basis. In one embodiment, the Group 11 metal content is 500 g/kg or less on the same basis. In one embodiment, the Group 11 metal content is 400 g/kg or less on the same basis.

Depositing Group 11 Metal on Spent Epoxidation Catalyst

Where the donee is spent epoxidation catalyst, and the Group 11 metal is silver, the amount of additional silver deposited on the donee generally is 0.2% w or more, based on the weight of the spent epoxidation catalyst. In one embodiment, the additional silver deposited is 0.5% w or more on the same basis. In one embodiment, the additional silver deposited is 1% w or more on the same basis. In one embodiment, the additional silver deposited is 5% w or more on the same basis. In one embodiment, the additional silver deposited is 8% w or more on the same basis. In one embodiment, the additional silver deposited is 10% w or more on the same basis. In one embodiment, the additional silver deposited is 12% w or more on the same basis.

General Group 11 Deposition Procedures

In one embodiment, rhenium is deposited on the donee with or subsequent to the deposition of the one or more Group 11 metal(s) or cationic Group 11 metal component(s). If cationic Group 11 metal component(s) are deposited, at least a portion of the cationic Group 11 metal component(s) is reduced.

The one or more Group 11 metals may be deposited on the donee by contacting the donee with a Group 11 metal deposition mixture. Suitable Group 11 deposition mixtures comprise a liquid containing dispersed Group 11 metal, for example a Group 11 metal sol. The method comprises removing the liquid, for example by evaporation, while leaving the one or more Group 11 metals on the donee. In an advantageous embodiment, the deposition mixture is a solution of compounds or complexes comprising the one or more Group 11 metals.

In an advantageous embodiment, the Group 11 metal is silver, and the deposition mixture is a silver deposition mixture. In this embodiment, the silver deposition mixture generally is a solution comprising one or more silver compounds or silver complexes.

The deposition may be carried out more than once, for example two times or three times, to accomplish the deposition of a desired amount of the one or more Group 11 metals. The Group 11 metal deposition mixture may comprise additives, such as dispersants and stabilizers. Such additives may be removed after the removal of the liquid, by heating for example, at a temperature of from 100 to 300° C., in particular from 150 to 250° C., in an inert atmosphere, for example in nitrogen or argon, or in an oxygen containing atmosphere, for example air or a mixture comprising oxygen and argon.

One or more cationic Group 11 metal components may be deposited on the donee by contacting the donee with a cationic Group 11 deposition mixture comprising liquid and the cationic Group 11 metal component. A liquid component of the cationic Group 11 deposition mixture is removed. A reducing agent may be applied prior to, together with or after the cationic Group 11 deposition mixture.

Typically, the cationic Group 11 deposition mixture may comprise the cationic Group 11 metal component and a reducing agent, in which case removing the liquid and performing reduction of at least a portion of the cationic Group 11 metal component may be accomplished simultaneously. Such deposition may be carried out more than once, for example two times or three times, to accomplish the deposition of a desired amount of cationic Group 11 metal. The cationic Group 11 metal component includes, for example, a non-complexed or complexed Group 11 metal salt, in particular, a cationic Group 11 metal-amine complex.

After the liquid component has been removed, the impregnated donee may be heated at a temperature of from 100 to 900° C., in particular from 150 to 300° C., in an inert atmosphere, for example in nitrogen or argon, or in an oxygen containing atmosphere, for example air or a mixture comprising oxygen and argon. The heating will, in general, effect the reduction of at least a portion of the cationic Group 11 metal-amine complex. Examples of cationic Group 11 metal-amine complexes are cationic Group 11 metal complexed with a monoamine or a diamine, in particular a 1,2-alkylene diamine. Examples of suitable amines are ethylene diamine, 1,2-propylene diamine, 2,3-butylene diamine, ethanol amine, and ammonium hydroxide. Higher amines may be used, such as, for example, triamines, tetraamines, and pentaamines. Examples of reducing agents are oxalates, lactates and formaldehyde.

For further particulars of cationic Group 11 deposition mixtures comprising cationic Group 11 metal-amine complex and a reducing agent, reference may be made to U.S. Pat. No. 5,380,697, U.S. Pat. No. 5,739,075, EP-A-266015, and U.S. Pat. No. 6,368,998, which are incorporated herein by reference.

A particularly advantageous silver deposition mixture includes, for example, a solution comprising additional cationic silver metal-amine complex. The preparation of an advantageous cationic silver metal-amine complex solution is described in Example 2.

The silver deposition mixture is contacted with the donee. The contact time may vary. Suitable contact times include, for example, 1 minute or more. In one embodiment, the contact time is 24 hours or less. The temperature and pressure may vary.

In an advantageous embodiment, the donee is evacuated as previously described and thereafter contacted with the Group 11 deposition mixture. In this embodiment, the contact time may be shortened. The temperature may be up to 95° C. In one embodiment, the temperature is in the range of from 10 to 80° C.

As an alternative, or in addition, the one or more Group 11 metals may be deposited on the donee by vapor deposition techniques known in the art.

Depositing One or More Rhenium Copromoters

The donee may or may not comprise a base amount of one or more rhenium copromoters.

Depositing One or More Rhenium Copromoters on Carrier Material for Fresh Epoxidation Catalyst In one embodiment, one or more rhenium copromoters are deposited on the carrier material for a fresh epoxidation catalyst.

The amount of rhenium copromoter deposited on the carrier material for a fresh epoxidation catalyst typically produces a total quantity of rhenium copromoter of 0.01 mmole/kg or more, based on the total weight of the fresh epoxidation catalyst. In one embodiment, the amount of rhenium copromoter deposited on the carrier material typically produces a total quantity of rhenium copromoter of 0.1 mmole/kg or more on the same basis. In one embodiment, the amount of rhenium copromoter deposited on the carrier material produces a total quantity of rhenium copromoter of 0.2 mmole/kg or more on the same basis.

In one embodiment, the amount of rhenium copromoter deposited on the carrier material produces a total quantity of rhenium copromoter of 200 mmole/kg or less on the same basis. In one embodiment, the amount of rhenium copromoter deposited on the carrier material produces a total quantity of rhenium copromoter of 50 mmole/kg or less on the same basis. In an advantageous embodiment, the amount of rhenium copromoter deposited on the carrier material produces a total quantity of rhenium copromoter of 25 mmole/kg or less, on the same basis.

Depositing One or More Rejuvenating Rhenium Copromoters on Spent Epoxidation Catalyst Where the donee is a spent epoxidation catalyst, the donee is rejuvenated. In this embodiment, the donee spent epoxidation catalyst may comprise a base amount of rhenium copromoter. In this embodiment, the rejuvenation process may deposit an additional amount of one or more rejuvenating rhenium copromoters on the donee.

Suitable rejuvenating rhenium copromoters may be selected from components comprising an element selected from tungsten, chromium, molybdenum, sulfur, phosphorus, boron, and mixtures thereof. Preferably, the rejuvenating rhenium copromoter is selected from components comprising tungsten, chromium, molybdenum, sulfur, and mixtures thereof. Advantageously, the rejuvenating rhenium copromoter comprises tungsten. An advantageous copromoter deposition mixture for depositing tungsten comprises an ammonium tungstate solution.

Where the donee is spent epoxidation catalyst, the quantity of each rejuvenating rhenium copromoter deposited on the donee spent epoxidation catalyst generally is 0.01 mmole/kg or more, based on the total weight of the rejuvenated epoxidation catalyst. In one embodiment, the amount of each rejuvenating rhenium copromoter deposited is 0.1 mmole/kg or more on the same basis. In one embodiment, the amount of each rejuvenating rhenium copromoter deposited is 40 mmole/kg or less on the same basis. In one embodiment, the amount of each rejuvenating rhenium copromoter deposited is 20 mmole/kg or less on the same basis. When the rejuvenating rhenium copromoter is molybdenum, the amount of rejuvenating molybdenum deposited may be 10 mmole/kg or less on the same basis.

Depositing One or More Further Elements

One or more further elements also may be deposited on the donee. The donee may or may not comprise a base amount of the one or more further elements.

Eligible further elements may be selected from the group of nitrogen, fluorine, alkali metals, alkaline earth metals, titanium, hafnium, zirconium, vanadium, thallium, thorium, tantalum, niobium, gallium, germanium, and mixtures thereof. Preferably the alkali metals are selected from sodium, lithium, potassium, rubidium, cesium, and mixtures thereof. Most preferably the alkali metals are selected from lithium, potassium, cesium, and mixtures thereof. Preferably the alkaline earth metals are selected from calcium, barium, magnesium, and mixtures thereof.

The further elements may be deposited in any form. For example, salts of alkali metals and/or alkaline earth metals are suitable. Suitable liquid further element deposition mixtures comprise the component(s) comprising one or more further elements dissolved or dispersed in a liquid. Suitable aqueous liquids and deposition procedures are described above with respect to rhenium. In an advantageous embodiment, the further element deposition mixture for depositing one or more alkali metals and/or one or more alkaline earth metals are metal hydroxide solutions.

The deposition of components comprising the further elements may be effected prior to, together with or subsequent to the deposition of other dopants. The quantities of various further elements that may be deposited on the donee are described below. As used herein, unless otherwise specified, the quantity of alkali metal present in an epoxidation catalyst is deemed to be the quantity insofar as it can be recovered from the epoxidation catalyst with de-ionized water at 100° C. The extraction method involves extracting a 10-gram sample of the epoxidation catalyst three times by heating it in 20 ml portions of de-ionized water for 5 minutes at 100° C. and determining in the combined extracts the relevant metals by using a known method, for example atomic absorption spectroscopy.

As used herein, unless otherwise specified, the quantity of alkaline earth metal present in an epoxidation catalyst is deemed to be the quantity insofar as it can be extracted from the epoxidation catalyst with 10% w nitric acid in de-ionized water at 100° C. The extraction method involves extracting a 10-gram sample of the catalyst by boiling it with a 100 ml portion of 10% w nitric acid for 30 minutes (1 atm., i.e. 101.3 kPa) and determining in the combined extracts the relevant metals using a known method, for example atomic absorption spectroscopy. Suitable extraction and measurement procedures are described, for example, in U.S. Pat. No. 5,801,259, which is incorporated herein by reference.

Depositing One or More Further Elements on Fresh Epoxidation Catalyst

Where the donee is a carrier material for preparing fresh epoxidation catalyst, the one or more further elements typically are deposited to produce a total quantity of 0.25 mmole/kg or more, based on the weight of the fresh epoxidation catalyst. In one embodiment, the one or more further elements are deposited to produce a total quantity of 100 mmole/kg or less on the same basis. The further elements may be provided in any form.

Depositing the One or More Rejuvenating Further Elements on Spent Epoxidation Catalyst Where the donee is spent epoxidation catalyst, with the exception of lithium, the amount of rejuvenating further elements may be 1 mmole/kg or more of the rejuvenated epoxidation catalyst. In one embodiment, the amount of rejuvenating further elements is 50 mmole/kg or less on the same basis.

When the rejuvenating further element comprises one or more alkali metals, the total amount of rejuvenating alkali metal, with the exception of lithium, generally is 0.1 mmole/kg or more on the same basis. In one embodiment, the total amount of rejuvenating alkali metal other than lithium is 0.2 mmole/kg or more on the same basis. In one embodiment, the total amount of rejuvenating alkali metal other than lithium is 50 mmole/kg or less on the same basis. In one embodiment, the total amount of rejuvenating alkali metal other than lithium is 30 mmole/kg or less on the same basis.

Where lithium is used as a rejuvenating alkali metal, the total amount of rejuvenating lithium is 1 mmole/kg on the same basis. In one embodiment, the total amount of rejuvenating lithium is 100 mmole/kg or less on the same basis.

Where rejuvenating cesium is deposited, the amount of rejuvenating cesium is 0.1 mmole/kg or more on the same basis. In one embodiment, the amount of rejuvenating cesium is 0.2 mmole/kg or more on the same basis. In one embodiment, the amount of rejuvenating cesium is 1 mmole/kg or more on the same basis. In one embodiment, the amount of rejuvenating cesium is 50 mmole/kg or less on the same basis. In one embodiment, the amount of rejuvenating cesium is 30 mmole/kg or less on the same basis. In one embodiment, the amount of rejuvenating cesium is 10 mmole/kg or less on the same basis.

Where rejuvenating alkaline earth metal is added, an advantageous amount of rejuvenating alkaline earth metal is 1 mmole/kg or more on the same basis. In one embodiment, the amount of rejuvenating alkaline earth metal is 100 mmole/kg or less on the same basis.

Methods for depositing the dopants on a carrier material are known in the art and such methods may be applied in the practice of the present process. Reference may be made to U.S. Pat. No. 5,380,697, U.S. Pat. No. 5,739,075, EP-A-266015, and U.S. Pat. No. 6,368,998, which are incorporated herein by reference. Suitably, such methods include impregnating the particulate carrier materials with a liquid mixture comprising cationic Group 11 metal-amine complex and a reducing agent.

A Rejuvenated Epoxidation Catalyst Exhibits Increased Selectivity, Increased Activity, or a Combination of Both Where the donee is spent epoxidation catalyst, the rejuvenation process produces rejuvenated epoxidation catalyst which exhibits increased selectivity, increased activity, or a combination thereof. As used herein, the selectivity is the quantity of olefin oxide formed, relative to the quantity of olefin converted, expressed in mole-%.

Advantageously, the rejuvenated epoxidation catalyst exhibits an increase in selectivity of 1-mole % or more, compared to selectivity of the donee spent epoxidation catalyst. In one embodiment, the rejuvenated epoxidation catalyst exhibits an increase in selectivity of 5 mole-% or more on the same basis. In one embodiment, the rejuvenated epoxidation catalyst exhibits an increase in selectivity of 7 mole-% or more on the same basis. More advantageously, the rejuvenated epoxidation catalyst exhibits an increase in selectivity of 10 mole-% or more on the same basis. Even more advantageously, the rejuvenated epoxidation catalyst exhibits an increase in selectivity of 12 mole-% or more on the same basis.

In one embodiment, the rejuvenated epoxidation catalyst exhibits an increase in activity compared to the donee spent epoxidation catalyst. Increased activity of the rejuvenated epoxidation catalyst is evidenced by a reduction in the temperature required to produce a given amount of alkylene oxide (the "production temperature"), compared to the production temperature of the donee spent epoxidation catalyst. A 5° C. reduction in the production temperature is the same as a 5° C. increase in activity.

In one embodiment, the production temperature of the rejuvenated epoxidation catalyst is reduced by 2° C. or more compared to the production temperature of the donee spent epoxidation catalyst. In one embodiment, the production temperature of the rejuvenated epoxidation catalyst is reduced by 3° C. or more on the same basis. In one embodiment, the production temperature of the rejuvenated epoxidation catalyst is reduced by 4° C. or more on the same basis. In one embodiment, the production temperature of the rejuvenated epoxidation catalyst is reduced by 5° C. or more on the same basis. In one embodiment, the production temperature is reduced by 8° C. or more on the same basis. In one embodiment, the production temperature is reduced by 9° C. or more on the same basis.

In one embodiment, the production temperature of the rejuvenated epoxidation catalyst is reduced by 40° C. or less on the same basis. In one embodiment, the production temperature of the rejuvenated epoxidation catalyst is reduced by 20° C. or less on the same basis. In one embodiment, the production temperature of the rejuvenated epoxidation catalyst is reduced by 15° C. or less on the same basis. In one embodiment, the production temperature of the rejuvenated epoxidation catalyst is reduced by 12° C. or less on the same basis. In one embodiment, the production temperature of the rejuvenated epoxidation catalyst is reduced by 10° C. or less on the same basis.

A spent epoxidation catalyst may be rejuvenated successive times after the epoxidation catalyst has been used again following an earlier rejuvenation. After completing a rejuvenation process, a feed comprising the olefin and oxygen may be reacted in the presence of the rejuvenated epoxidation catalyst using any suitable method.

The Carrier Material

Whether the donee is fresh carrier material or spent epoxidation catalyst, the epoxidation catalyst comprises a carrier material. The carrier material may be natural or artificial inorganic material, and may include refractory materials, silicon carbide, clays, zeolites, charcoal and alkaline earth metal carbonates, for example calcium carbonate. In an advantageous embodiment, the carrier material comprises one or more refractory materials. Examples of suitable refractory materials include, for example, alumina, magnesia, zirconia and silica. In an advantageous embodiment, the carrier material is $\alpha$-alumina. In this embodiment, the carrier material typically comprises at least 85% w, more typically at least 90% w, in particular at least 95% w $\alpha$-alumina, frequently up to 99.9% w $\alpha$-alumina, relative to the weight of the carrier. Other components of the $\alpha$-alumina may comprise, for example, silica, alkali metal components, for example sodium and/or potassium components, and/or alkaline earth metal components, for example calcium and/or magnesium components.

The surface area of the carrier material may suitably be at least 0.1 m$^2$/g, preferably at least 0.3 m$^2$/g, more preferably at least 0.5 m$^2$/g, and in particular at least 0.6 m$^2$/g, relative to the weight of the carrier; and the surface area may suitably be at most 10 m$^2$/g, preferably at most 5 m$^2$/g, and in particular at most 3 m$^2$/g, relative to the weight of the carrier. "Surface area" as used herein is understood to relate to the surface area as determined by the B.E.T. (Brunauer, Emmett and Teller) method as described in Journal of the American Chemical Society 60 (1938) pp. 309-316. High surface area carrier materials, in particular when they are an $\alpha$-alumina optionally comprising in addition silica, alkali metal and/or alkaline earth metal components, provide improved performance and stability of operation.

The water absorption of the carrier material is typically in the range of from 0.2 to 0.8 g/g, preferably in the range of from 0.3 to 0.7 g/g. A higher water absorption may be in favor in view of a more efficient deposition of one or more dopants. As used herein, water absorption is as measured in accordance with ASTM C20, and water absorption is expressed as the weight of the water that can be absorbed into the pores of the carrier, relative to the weight of the carrier.

The particulate carrier material may have a pore size distribution such that pores with diameters in the range of from 0.2 to 10 μm represent at least 70% of the total pore volume. Such relatively narrow pore size distribution can contribute to one or more of the activity, selectivity and longevity of the catalyst. Longevity may be in respect of maintaining the catalyst activity and/or maintaining the selectivity. As used herein, the pore size distribution and the pore volumes are as measured by mercury intrusion to a pressure of $3.0 \times 10^8$ Pa using a Micrometrics Autopore 9200 model (130° contact angle, mercury with a surface tension of 0.473 N/m, and correction for mercury compression applied).

In an advantageous embodiment, the pore size distribution is such that the pores with diameters in the range of from 0.2 to 10 μm represent more than 75%, in particular more than 80%, more preferably more than 85%, most preferably more than 90% of the total pore volume. Frequently, the pore size distribution is such that the pores with diameters in the range of from 0.2 to 10 μm represent less than 99.9%, more frequently less than 99% of the total pore volume.

In an advantageous embodiment, the pore size distribution is such that the pores with diameters in the range of from 0.3 to 10 μm represent more than 75%, in particular more than 80%, more preferably more than 85%, most preferably more than 90%, in particular up to 100%, of the pore volume contained in the pores with diameters in the range of from 0.2 to 10 μm.

Typically, the pore size distribution is such that pores with diameters of less than 0.2 μm represent less than 10%, in particular less than 5%, of the total pore volume. Frequently, the pores with diameters less than 0.2 μm represent more than 0.1%, more frequently more than 0.5% of the total pore volume.

Typically, the pore size distribution is such that pores with diameters greater than 10 μm represent less than 20%, in particular less than 10%, more in particular less than 5%, of the total pore volume. Frequently, the pores with diameters greater than 10 μm represent more than 0.1%, in particular more than 0.5% of the total pore volume.

Typically, the pores with diameters in the range of from 0.2 to 10 μm provide a pore volume of at least 0.25 ml/g, in particular at least 0.3 ml/g, more in particular at least 0.35 ml/g. Typically, the pores with diameters in the range of from 0.2 to 10 μm provide a pore volume of at most 0.8 ml/g, more typically at most 0.7 ml/g, in particular at most 0.6 ml/g.

The Epoxidation Process

The fresh or rejuvenated epoxidation catalyst may be used to catalyze an epoxidation process. The epoxidation process may be carried out in many ways. In one embodiment, the epoxidation process is a gas phase process, i.e., a process in which the feed is contacted in the gas phase with the epoxidation catalyst which is present as a solid material, typically in a packed bed. Generally the epoxidation process is a continuous process.

The olefin for use in the epoxidation process may be any olefin. Suitable olefins include aromatic olefins, for example styrene, or di-olefins, whether conjugated or not, for example 1,9-decadiene or 1,3-butadiene. Typically, the olefin is a monoolefin, for example 2-butene or isobutene. In one embodiment, the olefin is a mono-α-olefin, for example 1-butene or propylene. In an advantageous embodiment, the olefin is ethylene.

The olefin concentration in the feed to the epoxidation process may be selected within a wide range. Typically, the olefin concentration in the feed will be 80 mole % or less, relative to the total feed. In one embodiment, the olefin concentration will be from 0.5 to 70 mole %, relative to the total feed. In one embodiment, the olefin concentration will be from 1 to 60 mole %, relative to the total feed. As used herein, the feed is considered to be the composition which is contacted with the epoxidation catalyst.

The epoxidation process may be air-based or oxygen-based, see "Kirk-Othmer Encyclopedia of Chemical Technology", $3^{rd}$ edition, Volume 9, 1980, pp. 445-447. In an air-based process, air or air enriched with oxygen is employed as the source of the oxidizing agent while in an oxygen-based processes, high-purity (95 mole % or more) oxygen is employed as the source of the oxidizing agent.

The oxygen concentration in the feed may be selected within a wide range. However, in practice, oxygen is generally applied at a concentration which avoids the flammable regime. Typically, the concentration of oxygen applied will be from 1 to 15 mole %, more typically from 2 to 12 mole % of the total feed.

In order to remain outside the flammable regime, the concentration of oxygen in the feed may be lowered as the concentration of the olefin is increased. The actual safe operating ranges depend on the feed composition, and also on the reaction conditions such as the reaction temperature and the reaction pressure.

A reaction modifier may be present in the feed for increasing the selectively, suppressing the undesirable oxidation of olefin or olefin oxide to carbon dioxide and water, relative to the desired formation of olefin oxide. Many organic compounds, especially organic halides and organic nitrogen compounds, may be employed as the reaction modifier. Nitrogen oxides, hydrazine, hydroxylamine, ammonia, or combinations thereof may be employed as well. Without limiting the application to a theory, it is frequently considered that under the operating conditions of olefin epoxidation the nitrogen containing reaction modifiers are precursors of nitrates or nitrites, i.e., they are so-called nitrate- or nitrite-forming compounds (cf. e.g. EP-A-3642 and U.S. Pat. No. 4,822,900, which are incorporated herein by reference).

In an advantageous embodiment, the reaction modifiers are organic halides. Suitable organic halides include, for example, organic bromides and organic chlorides. In an advantageous embodiment, the organic halides are chlorohydrocarbons or bromohydrocarbons. In a particularly advantageous embodiment, the reaction modifiers are selected from the group of methyl chloride, ethyl chloride, ethylene dichloride, ethylene dibromide, vinyl chloride, and mixtures thereof. In a particularly advantageous embodiment, the reaction modifiers are ethyl chloride and ethylene dichloride.

Suitable nitrogen oxides are of the general formula $NO_x$ wherein x is in the range of from 1 to 2, and include for example NO, $N_2O_3$ and $N_2O_4$. Suitable organic nitrogen compounds are nitro compounds, nitroso compounds, amines, nitrates, and nitrites. Examples include nitromethane, 1-nitropropane or 2-nitropropane. In an advantageous embodiment, nitrate- or nitrite-forming compounds, e.g. nitrogen oxides and/or organic nitrogen compounds, are used together with an organic halide, in particular an organic chloride.

The reaction modifiers generally are effective when used at a concentration in the feed of, for example up to 0.1 mole %, relative to the total feed, for example from $0.01 \times 10^{-4}$ to 0.01 mole %. In an advantageous embodiment, where the olefin is ethylene, the reaction modifier is present in the feed at a concentration of from $0.1 \times 10^{-4}$ to $50 \times 10^{-4}$ mole %. In another advantageous embodiment, the reaction modifier is present in the feed at a concentration of from $0.3 \times 10^{-4}$ to $30 \times 10^{-4}$ mole %, relative to the total feed.

In addition to the olefin, oxygen, and the reaction modifier, the feed may contain one or more optional components, such as one or more of carbon dioxide, inert gases, and saturated hydrocarbons. Carbon dioxide is a by-product in the epoxidation process. However, carbon dioxide generally has an adverse effect on the catalyst activity. Typically, a concentration of carbon dioxide in the feed in excess of 25 mole %, relative to the total feed, is avoided. In an advantageous embodiment, a concentration of carbon dioxide in the feed in excess of 10 mole %, relative to the total feed, is avoided. A concentration of carbon dioxide as low as 1 mole % or lower, relative to the total feed, may be employed.

Inert gases, for example nitrogen or argon, may be present in the feed in a concentration of from 30 to 90 mole %, typically from 40 to 80 mole %.

Suitable saturated hydrocarbons which may be present in the feed include, for example, methane and ethane. If saturated hydrocarbons are present, they may be present in a quantity of 80 mole % or less, relative to the total feed. In an advantageous embodiment, saturated hydrocarbons are present in a quantity of 75 mole % or less, relative to the total feed. Frequently, saturated hydrocarbons are present in a quantity of 30 mole % or more, more frequently 40 mole % or more, relative to the total feed. Saturated hydrocarbons may be added to the feed in order to increase the oxygen flammability limit.

The epoxidation process may be carried out using reaction temperatures selected from a wide range. Advantageous reaction temperatures are in the range of from 150 to 325° C. In a particularly advantageous embodiment, the reaction temperatures are in the range of from 180 to 300° C.

Advantageously, the epoxidation process is carried out at a reactor inlet pressure in the range of from 1000 to 3500 kPa. "GHSV" or Gas Hourly Space Velocity is the unit volume of gas at normal temperature and pressure (0° C., 1 atm, i.e. 101.3 kPa) passing over one unit volume of packed catalyst per hour. Advantageously, when the epoxidation process is as a gas phase process involving a packed catalyst bed, the GHSV is in the range of from 1500 to 10000 Nl/(l·h). Advantageously, the process is carried out at a work rate of from 0.5 to 10 kmole olefin oxide produced per $m^3$ of catalyst per hour. In one embodiment, the process is carried out at a work rate of from 0.7 to 8 kmole olefin oxide produced per $m^3$ of catalyst per hour. In one embodiment, the process is carried out at a work rate of, for example, 5 kmole olefin oxide produced per $m^3$ of catalyst per hour. As used herein, the work rate is the amount of the olefin oxide produced per unit volume of catalyst per hour and the selectivity is the molar quantity of the olefin oxide formed relative to the molar quantity of the olefin converted.

The olefin oxide produced may be recovered from the reaction mixture by using methods known in the art, for example by absorbing the olefin oxide from a reactor outlet stream in water and optionally recovering the olefin oxide from the aqueous solution by distillation. At least a portion of the aqueous solution containing the olefin oxide may be applied in a subsequent process for converting the olefin oxide into a 1,2-diol or a 1,2-diol ether.

Conversion of Olefin Oxide into a 1,2-Diol, a 1,2-Diol Ether, or an Alkanolamine The olefin oxide produced in the epoxidation process may be converted by conventional methods into a 1,2-diol, a 1,2-diol ether, a 1,2-carbonate or an alkanol amine.

The conversion into the 1,2-diol or the 1,2-diol ether may comprise, for example, reacting the ethylene oxide with water, in a thermal process or by using a catalyst, which may be an acidic catalyst or a basic catalyst. For example, for making predominantly the 1,2-diol and less 1,2-diol ether, the olefin oxide may be reacted with a ten fold molar excess of water, in a liquid phase reaction in the presence of an acid catalyst, e.g. 0.5-1.0% w sulfuric acid, based on the total reaction mixture, at 50-70° C. at 100 kPa absolute, or in a gas phase reaction at 130-240° C. and 2000-4000 kPa absolute, preferably in the absence of a catalyst. The presence of such a large quantity of water may favor the selective formation of 1,2-diol and may function as a sink for the reaction exotherm, helping control the reaction temperature. If the proportion of water is lowered, the proportion of 1,2-diol ethers in the reaction mixture is increased. The 1,2-diol ethers thus produced may be a di-ether, tri-ether, tetra-ether or a subsequent ether. Alternative 1,2-diol ethers may be prepared by converting the olefin oxide with an alcohol, in particular a primary alcohol, such as methanol or ethanol, by replacing at least a portion of the water by the alcohol.

The olefin oxide may be converted into the corresponding 1,2-carbonate by reacting it with carbon dioxide. If desired, a 1,2-diol may be prepared by subsequently reacting the 1,2-carbonate with water or an alcohol to form the 1,2-diol. For applicable methods, reference is made to U.S. Pat. No. 6,080,897, which is incorporated herein by reference.

The 1,2-diols and 1,2 diol ethers, for example ethylene glycol, 1,2-propylene glycol and ethylene glycol ethers may be used in a large variety of industrial applications, for example in the fields of food, beverages, tobacco, cosmetics, thermoplastic polymers, curable resin systems, detergents, heat transfer systems, etc. The 1,2-carbonates, for example ethylene carbonate, may be used as a diluent, in particular as a solvent. Ethanol amines may be used, for example, in the treating ("sweetening") of natural gas.

Unless specified otherwise, the organic compounds mentioned herein, for example the olefins, alcohols, 1,2-diols, 1,2-diol ethers, 1,2-carbonates, ethanol amines and organic halides, have typically at most 40 carbon atoms, more typically at most 20 carbon atoms, in particular at most 10 carbon atoms, more in particular at most 6 carbon atoms. As defined herein, ranges for numbers of carbon atoms (i.e. carbon number) or for other parameters include the numbers specified for the limits of the ranges.

Suitable Reactors

The epoxidation process, the rhenium recovery process, and the dopant deposition process may be performed in any suitable reactor. Suitable reactors include, for example, one or more microchannel reactors, shell-and-tube heat exchanger reactors, stirred tank reactors, bubble columns or condensation apparatus. The present invention encompasses the use of such reactors or condensation apparatus, or the use of a plurality of reactors or condensation apparatus in these processes.

Advantageous reactors include, for example, reactors in the form of shell-and-tube heat exchangers and microchannel reactors. In an one embodiment, the process(es) are performed in the reaction tubes of a shell-and-tube heat exchanger reactor. In one embodiment, the process(es) are performed in an epoxidation reactor. This aspect eliminates the need for removing the epoxidation catalyst from the epoxidation reactor, and the catalyst may stay in place after the rejuvenation for use during a further period of production of the olefin oxide from the olefin and oxygen.

The following examples are intended to illustrate the advantages of the present invention and are not intended to unduly limit the scope of the invention, which is defined by the claims.

Example 1

Washing of Spent Catalyst

The following procedure was used to wash spent epoxidation catalyst to produce washed spent epoxidation catalyst. Where the spent epoxidation catalyst comprises rhenium, the wash may be used as an aqueous extract comprising rhenium. The unwashed or the washed spent epoxidation catalyst also is suitable for use as a donee for deposition of rhenium recovered from a donor spent epoxidation catalyst.

140 g of spent epoxidation catalyst was added to 202 grams of 0.03 w % ammonium nitrate solution. The temperature was brought up to 85° C. and held at 85±5° C. for 1 hour. The pellets of donee spent epoxidation catalyst were decanted and dried at 250° C. in flowing air for 15 minutes. The pellets were added to a fresh portion of 200 grams of 0.03 w % ammonium nitrate and heated for 1 hour at 87.5° C. (±5° C.). The ammonium nitrate solution was decanted and the pellets were soaked in 200 g of 0.03 w % ammonium nitrate solution at room temperature. The room temperature treatment was repeated one more time. Finally, the pellets were dried for 15 minutes at 250° C. This procedure removed most of the soluble dopants from the respective spent epoxidation catalyst and produced washed spent epoxidation catalyst.

Example 2

Preparation of Stock Silver Solution

A stock silver impregnation solution was prepared. In a 5-liter stainless steel beaker, 415 grams of reagent grade sodium hydroxide was dissolved in 2340 ml of deionized water. The temperature of the solution was adjusted to 50° C. In a 4-liter stainless steel beaker 1699 grams of silver nitrate was dissolved in 2100 ml of deionized water. The temperature of the solution was adjusted to 50° C. The sodium hydroxide solution was slowly added to the silver nitrate solution with stirring while the temperature was maintained at 50° C. The resulting slurry was stirred for 15 minutes. The pH of the solution was maintained at above 10 by the addition of NaOH solution as required. A liquid removal procedure was used which included removing liquid by the use of a filter wand followed by the replacement of the removed liquid with an equivalent volume of deionized water. This liquid removal procedure was repeated until the conductivity of the filtrate dropped below 90 micro-mho/cm. After the completion of the last liquid removal cycle, 1500 ml of deionized water was added and followed by the addition of 630 grams of oxalic acid dihydrate (4.997 moles) in increments of 100 grams while stirring and maintaining the solution at 40° C. (±5° C.). The pH of the solution was monitored during the addition of the last 130 grams of oxalic acid dihydrate to ensure that the pH did not drop below 7.8 for an extended period of time. Water was removed from the solution with a filter wand and the slurry was cooled to less than 30° C. Slowly added to the solution was 732 grams of 92 w % ethylenediamine (EDA). The temperature was maintained below 30° C. during this addition. A spatula was used to manually stir the mixture until enough liquid was present to mechanically stir the mixture.

Example 3

Donor spent epoxidation catalyst that had been in service for over one year was used in Examples 3 and 4. The donor spent epoxidation catalyst had a cumulative alkylene oxide production of 0.16 kT/m³ of spent epoxidation catalyst or more. A fixed amount of the donor spent epoxidation catalyst was boiled with a fixed amount of water and the rhenium-depleted donor was separated from the aqueous extract. The extracts were analyzed and rhenium concentration and recovery were calculated as a ratio of recovered rhenium to the total amount of rhenium initially present on the spent epoxidation catalyst.

In a first procedure, 100 g of the donor spent epoxidation catalyst was boiled in 100 g aliquots of water. 100 g of catalyst (containing 27.9 mg of Re) was placed in a beaker and 100 g of deionized water was added. The water was brought to a boil and the boiling was continued for 5 minutes. The beaker was then allowed to cool down to 50-60° C. and the liquid was decanted from the catalyst pellets. This process was repeated for a total of 3 times. The data is presented in the following Table:

| Extract No. | Re (mg recovered) | Combined Re recovery (%) | Combined extract concentration (mg/cc) | Extract recovered, grams |
|---|---|---|---|---|
| 1 | 17.4 | 62.3 | 0.28 | 58 |
| 2 | 7.82 | 90.3 (extr. 1 + 2) | 0.155 | 85 |
| 3 | 2.47 | 99.1 (extr. 1 + 2 + 3) | 0.104 | 85 |

Three extractions with water resulted in greater than 99% recovery of the rhenium.

Example 4

In a second procedure, 100 g of the catalyst of Example 3 (containing 27.9 mg of Re) was placed in a beaker and 200 g of deionized water was added. The water was brought to a boil and the boiling was continued for 5 minutes. The beaker was then allowed to cool down to 50-60° C. and the liquid was decanted from the catalyst pellets. The aqueous extracts were analyzed and rhenium concentration and recovery were calculated as a ratio of recovered rhenium to the total amount of rhenium initially present on the spent epoxidation catalyst. The data is presented in the following Table:

| Extract No. | Re (mg recovered) | Combined Re recovery (%) | Combined extract concentration (mg/cc) | Extract recovered, grams |
|---|---|---|---|---|
| 1 | 20.27 | 72.6 | 0.137 | 148 |

Using a larger amount of water for the extraction resulted in a higher recovery, but a more dilute extract solution.

PROPHETIC EXAMPLES

Prophetic Example 5

Preparation of Combined Deposition Mixture Comprising the Aqueous Extract from Example 3

The aqueous extract from Example 3 is evaporated and treated with an ammonium hydroxide solution to produce a rhenium deposition mixture comprising 0.02 g of $NH_4ReO_4$ in 2 g of 25% ammonium hydroxide.

A combined deposition mixture for rejuvenating a spent epoxidation catalyst is made by mixing the rhenium deposition mixture with: 150 grams of silver stock solution of specific gravity 1.6 g/cc; 0.06 g of ammonium metatungstate dissolved in 2 g of 1:1 ammonia/water; and, 0.2 g $LiOHxH_2O$ dissolved in water. Additional water is added to adjust the specific gravity of the solution to 1.5 g/cc. 50 grams of the resulting solution is mixed with 0.2 g of 50 w % CsOH solution, producing a combined deposition mixture.

Prophetic Example 6

Rejuvenation of Spent Epoxidation Catalyst Using the Combined Deposition Mixture of Example 5

Pellets of two donee spent epoxidation catalysts are subjected to a rejuvenation process. The donee spent epoxidation catalysts have a cumulative alkylene oxide production of 0.16 kT/m$^3$ of the spent epoxidation catalyst or more.

One of the spent epoxidation catalysts (Catalyst A) comprises α-alumina doped with silver, lithium, and cesium. The other spent epoxidation catalyst (Catalyst B) comprises α-alumina doped with silver, rhenium, tungsten, cesium, and lithium. The silver content of spent catalyst A is 15% w % or less, as determined by nitric acid digestion and silver titration. The extracted cesium content of spent catalyst A, after washing, is 70.

30 grams of pellets of washed spent catalyst A are evacuated to 20 mm Hg for 1 minute and the combined deposition mixture of Example 5 is added to the pellets while under vacuum. The vacuum is released and the resulting evacuated pellets of spent catalyst A are allowed to contact the combined deposition mixture for 3 minutes, producing an intermediate catalyst A. The pellets of intermediate catalyst A are then centrifuged at 500 rpm for 2 minutes to remove excess liquid. The resulting centrifuged pellets of intermediate catalyst A are placed in a vibrating shaker and dried in flowing air, producing rejuvenated catalyst A.

The final composition of the rejuvenated catalyst A pellets is determined. The rejuvenated catalyst A pellets comprise greater than 20 w % Ag, based on the total weight of rejuvenated catalyst A, and greater than 600 ppm of extracted Cs/g of the rejuvenated catalyst. The silver and extracted cesium content of the rejuvenated catalyst A pellets are determined as described above. The rejuvenated catalyst A pellets also comprise increased amounts of rhenium, tungsten, and lithium compared to spent catalyst A.

Performance Testing

Test Procedure

The various catalysts are tested to determine their catalytic properties, such as, selectivity and activity.

The following test procedure is used in the following Examples. The catalyst is crushed to 14 to 20 mesh size. 3 to 5 g of the crushed catalyst is loaded into a ¼ inch stainless steel U-shaped tube. The tube is immersed in a molten metal bath (heat medium) and the ends are connected to a gas flow system. The weight of catalyst that is used and the inlet gas flow rate are adjusted to give the specified gas hourly space velocity in normal liter/liter/hour (Nl/l/h), as calculated for uncrushed catalyst. As the catalyst packing density and silver loading change, the amount of catalyst loaded in the test reactor is changed.

Prophetic Example 7

Testing of Spent Catalyst A

The spent epoxidation catalyst that is rejuvenated to produce rejuvenated Catalyst A is tested for its ability to produce ethylene oxide from a feed containing ethylene and oxygen using the Test Procedure described above. The gas hourly space velocity is 3300 normal liter/liter/hour (Nl/l/h), as calculated for uncrushed catalyst. The catalyst loading is under 5 grams. The gas flow is 17 Nl/l/h. The inlet gas pressure is 1550 kPa. The results are given in Prophetic Example 8.

Prophetic Example 8

Testing of Rejuvenated Catalyst A

A testing gas mixture is passed through the catalyst bed using the test procedure described above. The testing gas mixture is 30% v ethylene, 8% v oxygen, 5% v carbon dioxide, 57% v nitrogen and 2.5 parts by million by volume (ppmv) ethyl chloride. The temperature is kept constant at 245° C. for 4 hours and then adjusted for the catalyst to stabilize and achieve 3.1 vol. % ethylene oxide (EO) production, based on the total volume of the testing gas. The catalyst loading is 4 grams. The gas flow is 17 Nl/l/h. The inlet gas pressure is 1550 kPa. The activity ° C. is substantially the same for spent Catalyst A and for rejuvenated Catalyst A. The selectivity of rejuvenated Catalyst A is 12% higher than that of spent Catalyst A.

Prophetic Example 9

Preparation of a Combined Deposition Mixture for Preparing Fresh Epoxidation Catalyst Comprising Extracted Rhenium The aqueous extract from Example 3 is evaporated and treated with an ammonium hydroxide solution to produce a rhenium deposition mixture comprising just under 0.05 g of NH$_4$ReO$_4$ in 2 g of 25% ammonium hydroxide.

A combined deposition mixture for making a fresh epoxidation catalyst is made by mixing the rhenium deposition mixture with: 50.0 grams of silver stock solution of specific gravity 1.6 g/cc; 0.01 g of ammonium metatungstate dissolved in 1 g of 1:1 ammonia/water; and, 0.05 g LiOHxH$_2$O dissolved in water. Additional water is added to adjust the specific gravity of the solution to 1.5 g/cc. 50.0 grams of the resulting solution is mixed with 0.1 g of 50 w % CsOH solution, producing a combined deposition mixture for preparing fresh epoxidation catalyst.

Prophetic Example 10

Preparation of Fresh Epoxidation Catalyst Using the Combined Deposition Mixture of Example 9

The fresh carrier used in this example has a water absorption of 50 cc/100 g. 30 grams of alpha alumina pellets are evacuated to 20 mm Hg for 1 minute and the combined deposition mixture of Example 9 is added to the pellets while under vacuum. The vacuum is then released and the resulting evacuated pellets of alpha alumina are allowed to contact the combined deposition mixture for 3 minutes, producing an intermediate fresh epoxidation catalyst. The pellets of intermediate fresh epoxidation catalyst are then centrifuged at 500 rpm for 2 minutes to remove excess liquid. The resulting centrifuged pellets of intermediate fresh epoxidation catalyst are placed in a vibrating shaker and dried in flowing air, producing fresh epoxidation catalyst.

The final composition of the fresh epoxidation catalyst is determined. The fresh epoxidation catalyst comprises 18 w % Ag, based on the total weight of the fresh epoxidation catalyst. The fresh epoxidation catalyst also produces over 500 ppm of extracted Cs/g of fresh epoxidation catalyst. The silver and extracted cesium content of the fresh epoxidation catalyst are determined as described above. The fresh epoxidation catalyst also comprises effective amounts of rhenium, tungsten, and lithium.

Prophetic Example 11

Testing of Fresh Epoxidation Catalyst

The fresh epoxidation catalyst prepared in Prophetic Example 10 is tested for its ability to produce ethylene oxide from a feed containing ethylene and oxygen using the test procedure described above. The fresh epoxidation catalyst exhibits a selectivity of 85% or more at a temperature of 250° C.

Persons of ordinary skill in the art will recognize that many modifications may be made to the foregoing description. The embodiments described herein are meant to be illustrative only and should not be taken as limiting the invention, which will be defined in the claims.

We claim:

1. A method for reusing rhenium from a donor spent epoxidation catalyst, the method comprising:
providing a donor comprising spent epoxidation catalyst comprising rhenium, the donor having a cumulative alkylene oxide production of 0.16 $kT/m^3$ of the spent epoxidation catalyst or more;
contacting the donor with an aqueous liquid to produce a rhenium-depleted donor and an aqueous extract comprising extracted rhenium;
separating the aqueous extract and the rhenium-depleted donor; and,
using the extracted rhenium as a source of rhenium in a subsequent process.

2. The method of claim 1 further comprising separating the extracted rhenium from the aqueous extract to produce recovered rhenium.

3. The method of claim 2 comprising removing diluent from the aqueous extract by a procedure selected from the group consisting of sublimation, distillation, concentration, and combinations thereof.

4. The method of claim 2 comprising passing the aqueous extract through a resin bed and collecting the recovered rhenium from the resin bed.

5. The method of claim 2 comprising depositing the recovered rhenium on a donee to form an epoxidation catalyst or an epoxidation catalyst precursor.

6. The method of claim 5 further comprising washing the donee before depositing the recovered rhenium on the donee.

7. The method of claim 1 further comprising depositing the extracted rhenium on a donee to form an epoxidation catalyst or an epoxidation catalyst precursor.

8. The method of claim 7 further comprising washing the donee before depositing the extracted rhenium on the donee.

9. The method of claim 7 comprising contacting the donee with a deposition mixture comprising the aqueous extract without first separating the extracted rhenium from the aqueous extract.

10. The method of claim 7 wherein the donee comprises spent epoxidation catalyst for preparing a rejuvenated epoxidation catalyst.

11. The method of claim 10 further comprising depositing silver on the donee in an amount of 0.2% w or more, based on the weight of the spent epoxidation catalyst.

12. The method of claim 10 further comprising depositing silver on the donee in an amount of 5% w or more, based on the weight of the spent epoxidation catalyst.

13. The method of claim 10 further comprising depositing on the donee one or more rejuvenating rhenium copromoter components selected from the group consisting of tungsten, chromium, molybdenum, sulfur, phosphorus, boron, and mixtures thereof.

14. The method of claim 10 further comprising depositing on the donee one or more rejuvenating further elements selected from the group consisting of nitrogen, fluorine, alkali metals, alkaline earth metals, titanium, hafnium, zirconium, vanadium, thallium, thorium, tantalum, niobium, gallium, germanium, and mixtures thereof.

15. The method of claim 10 further comprising depositing on the donee one or more rejuvenating alkali metals selected from the group consisting of lithium, cesium, and combinations thereof.

16. The method of claim 7 wherein the donee comprises a carrier material for preparing a fresh epoxidation catalyst.

17. The method of claim 16 further comprising depositing silver on the donee in a quantity of 10 g/kg or more, based on the weight of the fresh epoxidation catalyst.

18. The method of claim 16 further comprising depositing on the donee one or more rhenium copromoter components selected from the group consisting of tungsten, chromium, molybdenum, sulfur, phosphorus, boron, and mixtures thereof.

19. The method of claim 16 further comprising depositing on the donee one or more further elements selected from the group consisting of nitrogen, fluorine, alkali metals, alkaline earth metals, titanium, hafnium, zirconium, vanadium, thallium, thorium, tantalum, niobium, gallium, germanium, and mixtures thereof.

20. The method of claim 16 further comprising depositing on the donee one or more alkali metals selected from the group consisting of lithium, cesium, and combinations thereof.

21. The method of claim 1 wherein the donor has a cumulative alkylene oxide production of 0.2 $kT/m^3$ of the donor spent epoxidation catalyst or more.

22. The method of claim 1 wherein the donor has a cumulative alkylene oxide production of 1 $kT/m^3$ of the donor spent epoxidation catalyst or more.

23. The method of claim 1 wherein the aqueous liquid is selected from the group consisting of:
just water;
an aqueous liquid comprising one or more additives selected from salts, acids, bases, and peroxides;
an aqueous organic diluent; and,
mixtures thereof.

24. The method of claim 1 wherein the aqueous liquid consists of just water.

25. The method of claim 1 comprising
contacting a weight of the donor with a first aliquot of the aqueous liquid under first extraction conditions which extracts a first portion of rhenium from the donor, producing a first extracted donor and a first aqueous extract comprising a first amount of extracted rhenium; and,
contacting the first extracted donor with a second aliquots of the aqueous liquid under further extraction conditions which produces a second aqueous extracts comprising a second amounts of extracted rhenium.

26. The method of claim 25 wherein the first aliquot and second aliquots comprise substantially the same weight of the aqueous liquid as the weight of the donor.

27. The method of claim 1 wherein the total amount of extracted rhenium is 75% w or more of the total quantity of rhenium initially present on the donor.

* * * * *